(12) United States Patent
Zhang et al.

(10) Patent No.: US 10,617,782 B2
(45) Date of Patent: Apr. 14, 2020

(54) FLOWING FLUID DISINFECTION METHOD AND DISINFECTOR

(71) Applicant: BOLB INC., San Jose, CA (US)

(72) Inventors: Jianping Zhang, San Jose, CA (US); Ling Zhou, San Jose, CA (US); Ying Gao, San Jose, CA (US)

(73) Assignee: BOLB INC., San Jose, CA (US)

( * ) Notice: Subject to any disclaimer, the term of this patent is extended or adjusted under 35 U.S.C. 154(b) by 209 days.

(21) Appl. No.: 15/680,103

(22) Filed: Aug. 17, 2017

(65) Prior Publication Data

US 2019/0054201 A1 Feb. 21, 2019

(51) Int. Cl.
*A61L 2/10* (2006.01)
*A61L 9/20* (2006.01)
*C02F 1/32* (2006.01)

(52) U.S. Cl.
CPC ............... *A61L 9/20* (2013.01); *A61L 2/10* (2013.01); *C02F 1/325* (2013.01); *A61L 2202/11* (2013.01); *A61L 2202/14* (2013.01); *A61L 2202/21* (2013.01); *A61L 2209/111* (2013.01); *A61L 2209/12* (2013.01); *C02F 2201/328* (2013.01); *C02F 2201/3222* (2013.01); *C02F 2201/3228* (2013.01); *C02F 2301/02* (2013.01); *C02F 2301/022* (2013.01); *C02F 2303/04* (2013.01)

(58) Field of Classification Search
CPC ............... A61L 2/10; C02F 1/32; C02F 1/325
See application file for complete search history.

(56) References Cited

U.S. PATENT DOCUMENTS

| 6,447,721 | B1 | 9/2002 | Horton, III et al. | 422/24 |
| 7,601,960 | B2 | 10/2009 | Albrecht et al. | 250/365 |
| 8,795,600 | B2 | 8/2014 | Byers et al. | 422/186.3 |
| 2003/0089670 | A1 | 5/2003 | Saccomanno | 210/748 |
| 2007/0119922 | A1* | 5/2007 | Levy | A61L 2/10 235/380 |
| 2008/0265179 | A1* | 10/2008 | Havens | A61L 2/10 250/492.1 |
| 2015/0158750 | A1* | 6/2015 | Schiffmann | C02F 1/32 210/739 |
| 2018/0305226 | A1* | 10/2018 | Simpson | C02F 1/325 |

OTHER PUBLICATIONS

"UV Irradiation Dosage Table" American Air & Water—http://www.americanairandwater.com/uv-facts/uv-dosage.htm.
"Ultraviolet Light Disinfection Data Sheet" CD ClorDiSys—http://www.clordisys.com/pdfs/misc/UV%20Data%20Sheet.pdf.

* cited by examiner

*Primary Examiner* — Donald R Spamer
(74) *Attorney, Agent, or Firm* — J.C. Patents

(57) ABSTRACT

A method for disinfecting a fluid includes emitting UV light into a flowing fluid pillar along its axial direction. The flowing fluid pillar is surrounded by and in contact with a fluid medium having a refractive index lower than that of the fluid to be disinfected so that total internal reflection occurs when the UV light travels within the flowing fluid pillar. Also provided is a UV disinfector for disinfecting a flowing fluid.

10 Claims, 10 Drawing Sheets

UV dosage: $J = \int_0^L \frac{P}{S} e^{-\alpha x} \frac{dx}{v}$ $J = \frac{P}{S\alpha v}(1 - e^{-\alpha L})$ $J = \frac{P}{\alpha G}(1 - e^{-\alpha L}), G = Sv$ $L = -\frac{1}{\alpha}\ln(1 - \frac{J\alpha G}{P})$

FLOWING FLUID DISINFECTION METHOD AND DISINFECTOR

FIELD OF THE INVENTION

The present invention relates in general to flowing fluid disinfection and, more particularly to a flowing fluid disinfection method adopting deep UV light emission for improved fluid disinfection efficacy and a disinfector to realize the same.

DESCRIPTION OF THE RELATED ART

Non-chemical fluid disinfection is highly desirable in food, beverage and medicine industries as germicidal chemicals possess certain health concerns. In the prior art, low-pressure mercury lamps are occasionally used for this purpose, as their 254-nm UVC emissions (light emissions between 100 nm-280 nm are classified into UVC band, light emissions between 280 nm-315 nm are classified into UVB band) are efficient in germicidal effect. The germicidal effect arises from damages to microorganisms' DNA/RNA by UVC photons, since heavily damaged DNA/RNA cannot duplicate itself, leading to severe suppression and even elimination of microorganisms' reproduction. Data plotted in FIG. 1 summarize some prior art UVC 254-nm line's germicidal effective dosages for some common microorganisms (on-line data source, e.g. http://www.americanairandwater.com/uv-facts/uv-dosage.htm, and http://www.clordisys.com/pdfs/misc/UV%20Data%20Sheet.pdf, and references therein). As seen, for most of these microorganisms (e.g. *Escherichia Coli* and *Salmonella Enteritidis* et al), a 254 nm UV dosage of ~10 mJ/cm$^2$ can result in a sterilization effect by killing almost all microorganisms (5 log-reduction). By increasing the dosage to 20 mJ/cm$^2$, even the tough bacteria like Sarcina *Lutea* can be severely suppressed from reproduction.

The prior art UV fluid disinfection technology and apparatuses can be found in many patents and references therein, for example, U.S. Pat. Nos. 6,447,721, 7,601,960, 8,795,600 and US20030089670.

On the other hand, a new technological approach using UVC light emissions from solid-state semiconductor emitters is very promising for fluid disinfection. As known, nitride compound semiconductors such as AlInGaN dependent on alloy composition enable ultraviolet (UV) emissions ranging from 410 nm down to approximately 200 nm. This facilitates the best UV germicidal wavelength selection, which occurs at 265-270 nm and corresponds to a maximum UV absorption by microorganisms' DNA. Moreover, solid-state AlInGaN UV emitters, such as light-emitting diodes (LEDs) being non-toxic and robust by nature, can offer fast light on/off switch (cutoff frequency up to 200 MHz) and far higher UVC light intensity. Solid-state devices' intrinsic compact footprint further opens design versatility for various application scenarios. These merits make AlInGaN UVC LEDs the ideal light source for sterilization and disinfection, especially for fluids.

However, in addition to other disadvantages, current fluid disinfection technology suffers UV energy loss caused by the fluid-solid interface between the fluid to be disinfected and the device containing the fluid.

SUMMARY OF THE INVENTION

The present invention provides a method and a disinfector for flowing fluid disinfection/sterilization, in which, a flowing fluid pillar is generated with its sidewall being surrounded by and in direct contact with a fluid medium, UV light such as UVC light is emitted into the flowing fluid pillar along axial direction. By eliminating the fluid-solid interface between the fluid to be disinfected and the disinfector containing the fluid, UV energy loss can be reduced and disinfection efficacy for flowing fluid such as water, beverages or medical fluids can be improved.

One aspect of the present invention provides a method for disinfecting a fluid. The method includes:
providing a fluid to be disinfected;
generating a flowing fluid pillar of the fluid to be disinfected, wherein sidewall of the flowing fluid pillar is surrounded by and in contact with a fluid medium having a refractive index lower than that of the fluid to be disinfected; and emitting UV light into the flowing fluid pillar along an axial direction of the flowing fluid pillar.

Optionally, the fluid medium can be air or vacuum, the flowing fluid pillar can be a laminar flow pillar.

The method can further include:
determining a light path length of the UV light, L, according to the following equation:

$$L = -\frac{1}{\alpha}\ln\left(1 - \frac{J\alpha G}{P}\right)$$

where α is UV light absorption coefficient of the fluid to be disinfected, G is flow rate of the flowing fluid pillar, P is UV light power of the UV light impinging substantially vertically to a cross-section of the flowing fluid pillar, J is UV dosage experienced by the fluid in the flowing fluid pillar; and
determining a length of the flowing fluid pillar according to the light path length of the UV light.

Optionally, the length of the flowing fluid pillar can be equal to or larger than the light path length of the UV light.

Optionally, when a UV reflecting mirror is adopted at the other end of the flowing fluid pillar facing against the UV light source, the length of the flowing fluid pillar can be equal to or less than the light path length of the UV light.

Optionally, the UV light source can be an AlGaN based UVB or UVC LED light source.

Generally, the length of the flowing fluid pillar can be in the range of 10 to 500 cm. Another aspect of the present invention provides a UV disinfector. The UV disinfector includes:
a UV light source; and
a laminar flow injector comprising a housing for accommodating a fluid to be disinfected, the housing having a nozzle for generating therethrough a flowing fluid pillar of the fluid to be disinfected;
wherein the housing of the laminar flow injector has an outlet chamber connected with the nozzle, an inlet chamber connected with an inlet of the housing, and a laminar flow enforcer located between the inlet chamber and the outlet chamber, the laminar flow enforcer helps to generate a laminar flow in the flowing fluid pillar;
wherein the UV light source and the laminar flow injector are so configured that, when in use, UV light is emitted from the UV light source into the flowing fluid pillar and travels within the flowing fluid pillar along an axial direction of the flowing fluid pillar, and the flowing fluid pillar is preferred to be a laminar flowing fluid pillar.

The UV light source can be mounted in the housing of the laminar flow injector, an emitting surface of the UV light source is exposed to the outlet chamber and aligned with the nozzle.

The UV disinfector can further include a germicidal housing having a germicidal chamber for receiving the flowing fluid pillar, wherein, when in use, there is a gap between an inner sidewall of the germicidal housing and a sidewall of the flowing fluid pillar.

The UV light source can be mounted to the germicidal housing and, when in use, an emitting surface of the UV light source is exposed to and in contact with a distal end of the flowing fluid pillar.

A UV mirror can be mounted to the germicidal housing for reflecting UV light traveling through the flowing fluid pillar and, when in use, the UV mirror is exposed to and in contact with a distal end of the flowing fluid pillar.

BRIEF DESCRIPTION OF THE DRAWINGS

The accompanying drawings, which are included to provide a further understanding of the invention and constitute a part of this application, illustrate embodiments of the invention and together with the description serve to explain the principle of the invention. Like reference numbers in the figures refer to like elements throughout, and a layer can refer to a group of layers associated with the same function.

DETAILED DESCRIPTION OF EMBODIMENTS

Figure 1:
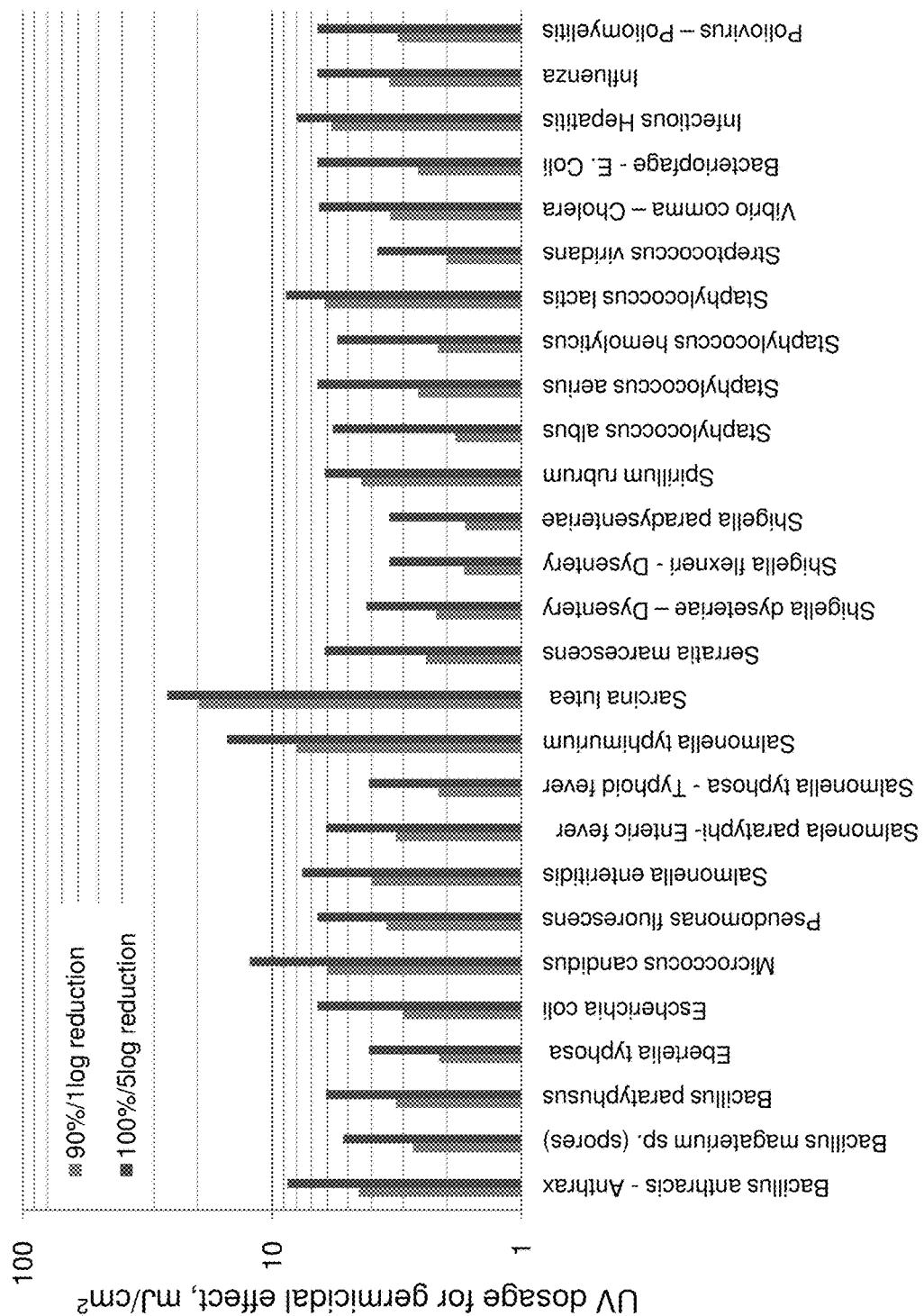
FIG. 1 plots the 254-nm UVC germicidal dosages for some common microorganisms. Grey bars and black bars represent for one-log and 5-log reduction, respectively.

As shown in FIG. 1, for most common microorganisms, a successful germicidal/disinfection/sterilization effect takes place at UVC dosage of ~10 mJ/cm$^2$, and a tough bacterium may need dosage more than 20 mJ/cm$^2$. Note that these dosage data are for 254 nm UVC light. As for 265-270 nm UVC light, the required UV dosage can be even less, since 265-270 nm light has better germicidal effectiveness (40% to 100% better) than 254 nm light. Generally speaking, the more the UVC dosage is applied, the better the disinfection effectiveness is. Since dosage is the product of light power intensity and light duration time, the method to control dosage is straightforward.

Figure 2:
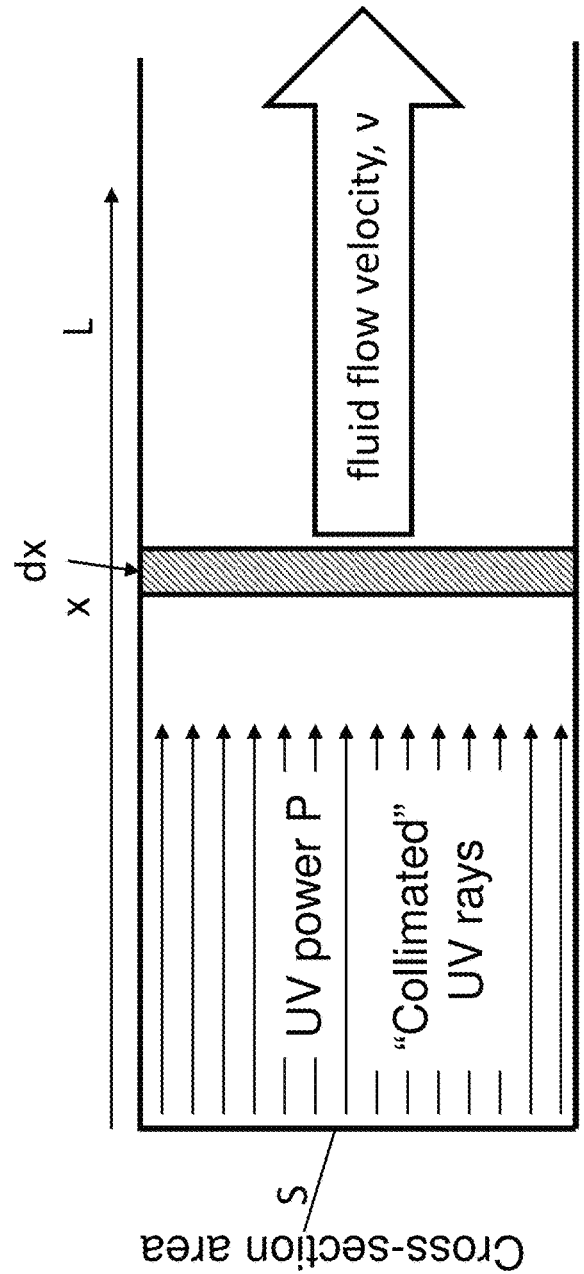
FIG. 2 illustrates the calculation of UV dosage in a flowing fluid pillar.

Consider a flowing fluid pillar with cross-sectional area S, UVC absorption coefficient α, flow rate G and flow velocity v, with input UVC light power P uniformly impinging vertically to the cross-section (i.e., the emitting angle β of the UV light is zero) and parallel to the flow direction (flow axial direction), as illustrated in FIG. 2. The UVC dosage experienced by the fluid is J, and $$J = \int_0^L \frac{P}{S} e^{-\alpha x} \frac{dx}{v},$$

where L is the UVC light path length. Solving the integration equation leads to $$J = \frac{P}{S\alpha v}(1 - e^{-\alpha L}).$$

Since G=Sv, so arrives at, $$J = \frac{P}{\alpha G}(1 - e^{-\alpha L}), \text{ and,} \qquad \text{eq \#1,}$$

$$L = -\frac{1}{\alpha}\ln\left(1 - \frac{J\alpha G}{P}\right), \qquad \text{eq \#2.}$$

Eq #1 can calculate UVC dosage if UVC light power, light path length, fluid flow rate, and fluid UVC absorption coefficient are known. Or more usefully, eq #2 can determine a light path length if a target dosage is set and the UVC light power, fluid flow rate and absorption coefficient are given. This is very important for designing a flowing fluid UVC light disinfector, as seen in the following context and from the data plotted in FIG. 4.

Figure 3:
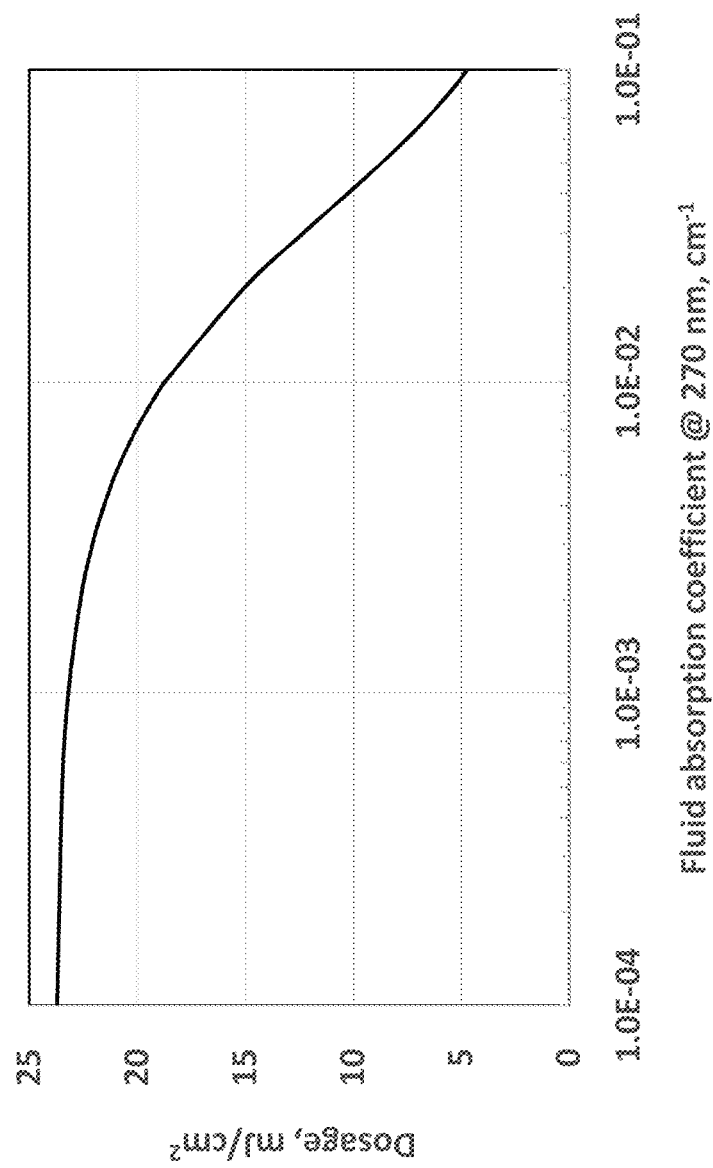
FIG. 3 plots for a given flow rate (10 gallon/min), UVC light power (300 mW) and light path length (50 cm) the UVC dosage function against fluid UVC absorption coefficient.

FIG. 3 plots for a given flow rate (10 gallon/min), UVC light power (300 mW) and light path length (50 cm) the UVC dosage function against fluid UVC absorption coefficient. As seen, once the fluid becomes more UVC absorbing (α>0.01 cm$^{-1}$), the delivered UVC dosage is fast decreasing. However, for absorption coefficient less than 0.01 cm$^{-1}$, the dosage change is rather small.

Figure 4:
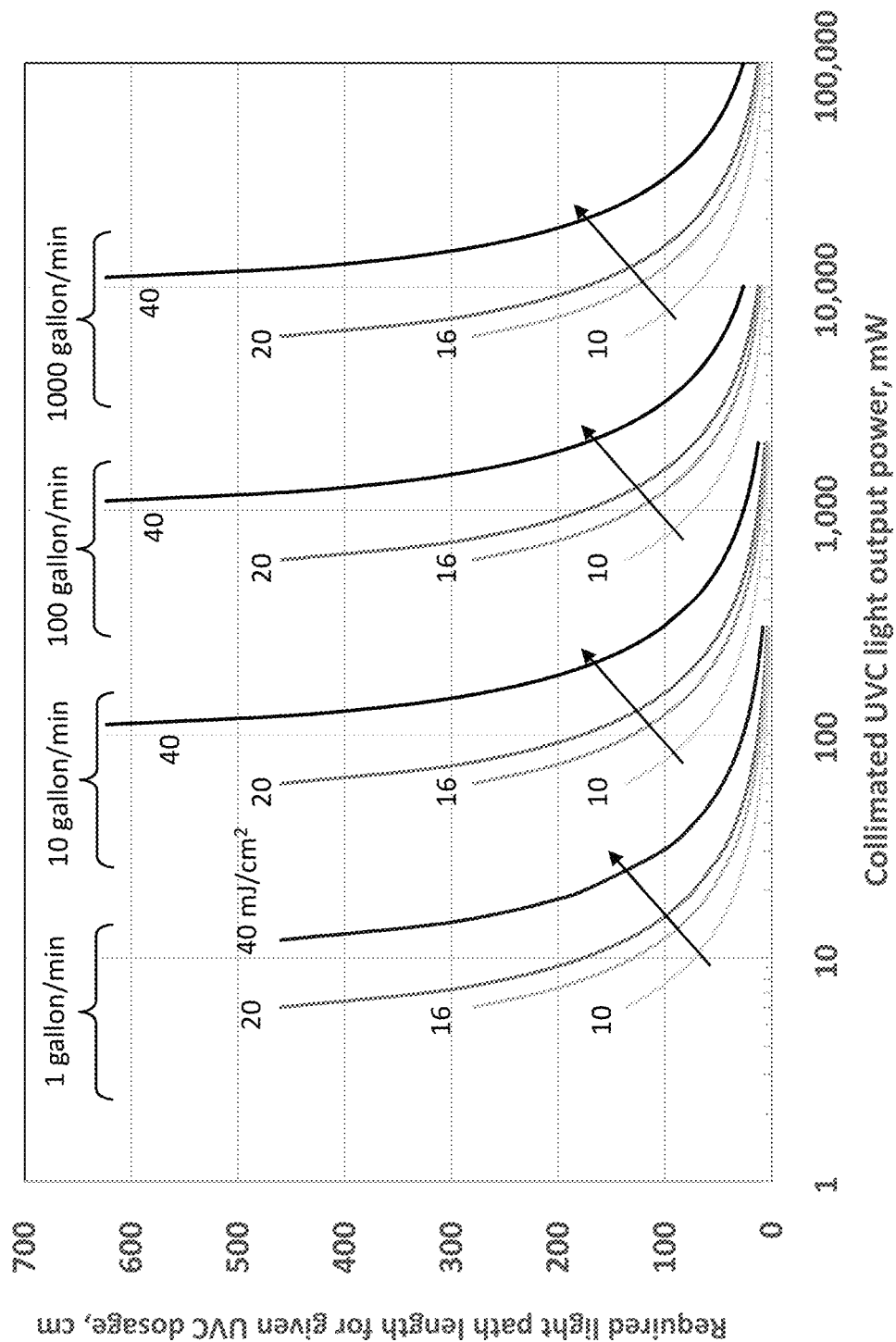
FIG. 4 plots for a given UVC absorption coefficient (0.004 cm$^{-1}$) and target germicidal dosages (10, 16, 20, 40 mJ/cm$^2$) the required light path lengths as functions of UVC light powers (1-100,000 mW) and fluid flow rates (1, 10, 100, 1000 gallon/min).

FIG. 4 plots for a given UVC absorption coefficient (0.004 cm$^{-1}$) and target germicidal dosages (10, 16, 20, 40 mJ/cm$^2$) the required light path lengths as functions of UVC light powers (1-100,000 mW) and fluid flow rates (1, 10, 100, 1000 gallon/min). As seen, larger flow rate requires more UVC light power to achieve the same UVC dosage. For example, for the same light path length of 50 cm, a 1 gallon/min flow rate only requires 14 mW UVC light power to gain a dosage of 10 mJ/cm$^2$; while a 10 gallon/min flow under the same conditions requires 140 mW UVC light power. Further, for a target UVC dosage, the longer the light path length, the less the UVC light input power is required. For example, for a target dosage of 20 mJ/cm$^2$, a UVC power of 280 mW with a light path length of 50 cm will do the job, meanwhile, a UVC power of 80 mW with light path length of 250 cm will do the same job.

Please note that the NSF (National Sanitation Foundation) Standard 55-1991 Ultraviolet Microbiological Water Treatment Systems demand the NSF failsafe set-point dosage for Class A systems UVC water treatment system is 40 mJ/cm$^2$, and International Water-Guard designs its Class A units to operate at a minimum dosage of 40 mJ/cm$^2$ as well. Class A systems are those designed to disinfect water contaminated by micro-organisms like bacteria and viruses, but not water with an obvious contamination source such as raw sewage, nor are they designed to convert wastewater to safe drinking water. Class B systems are intended to provide supplemental treatment of drinking water that has been tested by health authorities and deemed acceptable for human consumption. These systems are targeted at nonpathogenic and nuisance organisms. The NSF dosage requirement for Class B systems is 16 mJ/cm$^2$.

For example, to design a Class B water treatment system with flow rate of 1 gallon/min, if the UVC light output power is 50 mW then a light path length of 21 cm is required; and to design a Class A water treatment system with flow rate of 1 gallon/min, if the UVC light output power is 50 mW then a light path length of 56.4 cm is required; and to design a Class A water treatment system with flow rate of 1 gallon/min, if the UVC light output power is 100 mW then a light path length of 26.6 cm is required, et al, according to the calculations given in FIG. 4.

The calculated curves in FIG. 4 also teach that in general, through proper design, a few tens of mW UVC power is capable of disinfecting a 1 gallon/min flowing fluid; a few hundreds of mW UVC power is capable of disinfecting a 10 gallon/min flowing fluid; a few watts UVC power is capable of disinfecting a 100 gallon/min flowing fluid; and a few tens of watts UVC power is capable of disinfecting a 1000 gallon/min flowing fluid. This means that UVC LEDs are capable of disinfecting flowing fluids such as water for household, small community and even industrial applications. Generally speaking, according to FIG. 4, the UV light power and the flow rate of the flowing fluid pillar can be in the following range: a power of the emitted UV light is in the range of 30-70 mW and a flow rate of the flowing fluid pillar is in the range of 0.5-1.5 gallon/min; a power of the emitted UV light is in the range of 300-700 mW and a flow rate of the flowing fluid pillar is in the range of 5-15 gallon/min; or a power of the emitted UV light is in the range of 3-7 watts and a flow rate of the flowing fluid pillar is in the range of 50-150 gallon/min; or a power of the emitted UV light is in the range of 30-70 watts and a flow rate of the flowing fluid pillar is in the range of 500-1500 gallon/min.

To obtain the ideal disinfection curves (such as those shown in FIG. 4) and utilize the full potential of the UVC germicidal effect, a disinfection apparatus has to maximize UVC light path length and minimize light loss due to absorptions by interfaces and objects other than microorganisms.

According to an embodiment of the present invention, a flowing fluid pillar of a fluid to be disinfected is generated, and UV light is emitted into the flowing fluid pillar and travels along its axial direction. The flowing fluid pillar has a stable side surface, the side surface is surrounded by and in direct contact with a medium having a refractive index lower than that of the fluid to be disinfected. The medium can be a gas such as air gas, or any other suitable gas or a mixture thereof, which can be under high pressure, normal pressure, or low pressure, or the flowing fluid pillar can be generated in vacuum. By surrounding the flowing fluid pillar with such a medium, a total internal reflection of the UV light traveling within the flowing fluid pillar can be achieved by controlling the incident angel of UV light, so that absorption of UV light by the interface can be eliminated or significantly reduced. Desirably, but not limited to, the flowing fluid pillar can be a laminar flow. In an embodiment, the flowing fluid pillar flows along a substantially straight line. In another embodiment, the flowing fluid pillar flows along a slightly curved path (for example, naturally occurred due to gravity). Particles or other UV absorption materials can be filtered out from the fluid to be disinfected before forming the flowing fluid pillar. The flowing fluid pillar can flow vertically downward, horizontally, or in any other desired direction. The downstream end of the flowing fluid pillar can be stopped by a receiving surface such as a UV reflection mirror, a UV reflection film, or a UV light emitting surface, or beyond the downstream end the flowing fluid pillar can continue as a free flow.

The UV light source can be any conventional UV light source as long as directional light beam can be generated, such as LED, laser, or low-pressure mercury lamp. In use, light emitted from a UV light source is regulated into a directional light beam such as collimated or quasi-collimated light beam, the directional UV light travels within the flowing fluid pillar along the axial direction of the flowing fluid pillar. Desirably, the angle between the UV light ray and the axis of the flowing fluid pillar is in the range of 0 to $(90-\theta_c)$, where $\theta_c$ is the critical incident angle, $\theta_c$=arcsine $(n_1/n_2)$, $n_1$ is the refractive index of the medium surrounding the flowing fluid pillar, $n_2$ is the refractive index of the fluid in the flowing fluid pillar. Within such an angle range, total internal reflection will occur. The UV light can enter the flowing fluid pillar either from upstream end or downstream end of the flowing fluid pillar.

The disinfector according to embodiments of the present invention includes a fluid injector for generating a flowing fluid pillar such as a laminar flowing fluid pillar. A UV light source can be installed in the fluid injector for emitting UV light into the flowing fluid pillar. The disinfector may include a germicidal chamber located downstream of the fluid injector for housing the flowing fluid pillar and/or collecting disinfected fluid. In an embodiment, a UV light source is provided at the germicidal chamber for emitting UV light into the flowing fluid pillar from its downstream end.

Figure 5A:
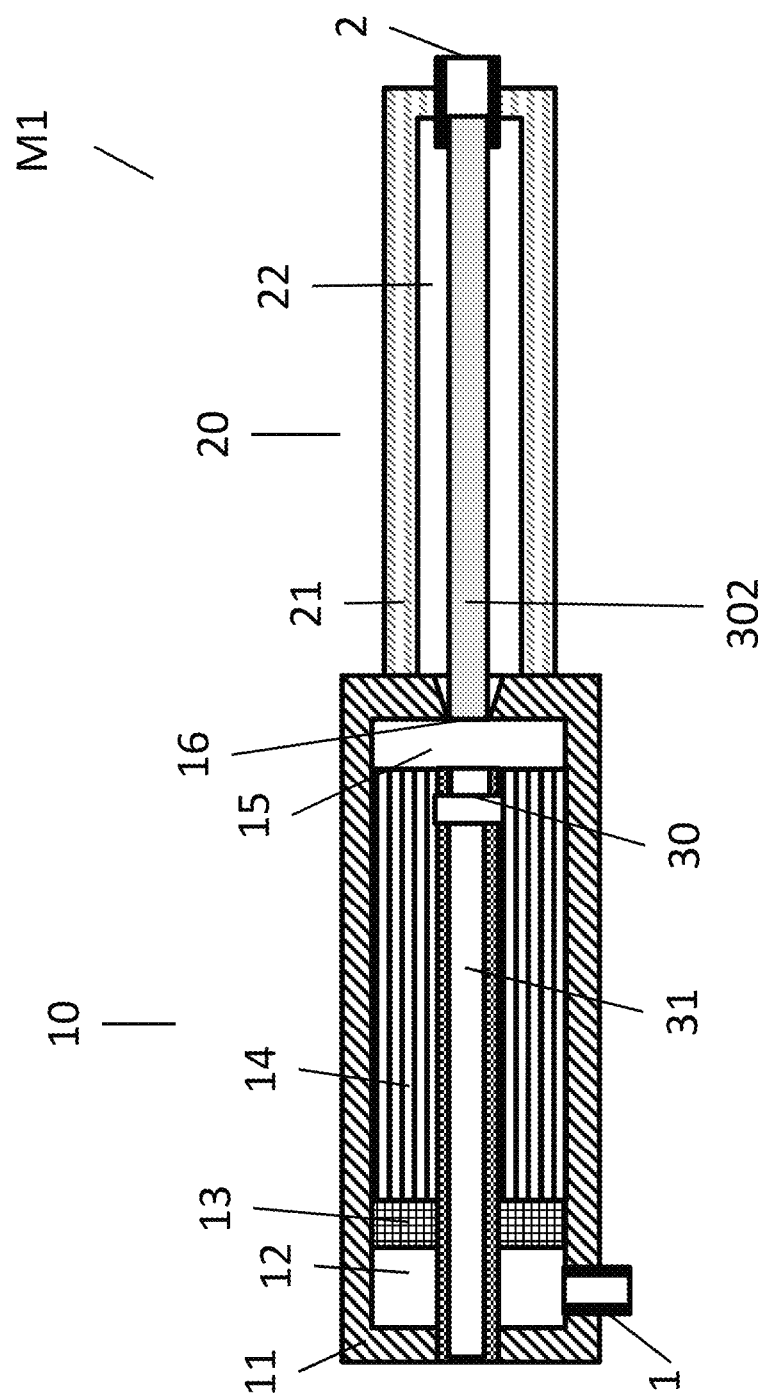
FIG. 5A shows an illustrative cross-sectional view of a flowing fluid UV disinfector module according to an embodiment of the present invention.

Shown in FIG. 5A is an illustrative cross-sectional view of a flowing fluid UV disinfector designed to reflect these merits according to an embodiment of the present invention. Referring to FIG. 5A, disinfector M1 has a germicidal chamber 20, a fluid laminar flow injector 10 and a UVC LED module 30. The germicidal chamber 20 contains a germicidal chamber housing 21, an air spacer 22, a fluid outlet 2. A laminar flowing fluid pillar 302 coupled with UVC light is generated, which will be discussed in details in the following. The fluid laminar flow injector 10 includes a fluid inlet 1, an injector chamber housing 11, an inlet chamber 12, a turbulence remover 13, a laminar flow enforcer 14, an outlet chamber 15, a nozzle 16, and a UVC LED module passway 31 for accommodating the UVC LED module 30. The purpose of fluid laminar flow injector 10 is to convert an inlet flow into a laminar flow substantially with no turbulence and bubbles therein. From left to right in FIG. 5A, an inlet fluid flow passes through fluid inlet 1 into inlet chamber 12, which has a much larger cross-sectional area than that of fluid inlet 1, so as to buffer the fluid flow and let the flow be coarsely filtered by turbulence remover 13 to remove particles and more importantly to remove or reduce turbulence within the inlet flow. For this purpose, turbulence remover 13 can be a layer or many layers of coarse fluid filters radially disposed, the coarse fluid filter can be a sediment filter or a particle filter with micro-mesh. Laminar flow enforcer 14 then turns the inlet flow into a laminar flow, substantially free of turbulence and bubbles. Laminar flow enforcer 14 can be made of densely packed, straight, parallel small tubes of lengths exceedingly larger than their cross-sectional dimensions, for example, the length-diameter ratio of the tube can be in the range of 10-100. The tube shown in FIG. 5A has a cylindrical shape, the tube may also have other shape such as rectangle or square cross section. The diameter of any individual tube may be in the range of 0.05-0.3 inch such as 0.1 inch and its length can be in the range of 0.6-6 inch such as 1, 4, or 5 inch. In an embodiment, the diameter of the tube is 0.1 inch and the length of the tube is 3 inch. Desirably, all the tubes have the same cross sectional shape and dimension. The space, if any, between the tubes is sealed so that no fluid flows therethrough. Laminar flow enforcer 14 divides fluid flow into many sub-flows and enforce these sub-flows to flow straight and in parallel, thus turn the fluid into laminar flow. And the laminar flow is then buffered in outlet chamber 15 before it shoots out through nozzle 16 to form a laminar flowing fluid pillar 302. Nozzle 16 is formed at the downstream side of outlet chamber 15 on injector chamber housing 11. The nozzle aperture contacting the fluid in outlet chamber 15 determines the cross-section of an outgoing flow (e g laminar flowing fluid pillar 302), and the aperture quickly and smoothly opens up (increases its opening radius) in the direction of the flow to reduce contact area of laminar flowing fluid pillar 302 and nozzle 16. This will help the formation of a smooth and steady laminar flowing fluid pillar 302. Further, the nozzle aperture can be made adjustable with smooth contacting surface with laminar flowing fluid pillar 302. For example, there can have a set of nozzles having difference aperture sizes, and a knob switch can be turned to select different nozzles. In this case (not shown in FIG. 5A), nozzle 16 may not be formed in injector chamber housing 11, and is separated but in fluid-tight such as water-tight connection to injector chamber housing 11. This feature allows for flexibility to adjust the length of laminar flowing fluid pillar 302, in cases the inlet fluid flow rate changes. In another embodiment, the nozzle aperture may also have a constant opening radius. Desirably laminar flowing fluid pillar 302 is substantially free of bubbles, turbulence, spraying and shaking for maximal light path length of UVC light trapped therein. Had flowing fluid pillar 302 been non-laminar, UVC light traveling within the flowing fluid pillar would have experienced scattering and loss due to the presence of turbulence and bubbles. Laminar flowing fluid pillar 302 is separated from germicidal chamber housing 21 by air spacer 22. Air spacer 22 surrounds and is in direct contact with sidewall of laminar flowing fluid pillar 302 to prevent the sidewall of laminar flowing fluid pillar 302 from contacting the inner surface of germicidal chamber housing 21.

In the embodiment shown in FIG. 5A, germicidal chamber housing 21 is connected to injector chamber housing 11 for receiving flowing fluid pillar 302. Germicidal chamber housing 21 can be fixedly or detachably attached to injector chamber housing 11, or germicidal chamber housing 21 and injector chamber housing 11 can be formed integrally. In other embodiments, germicidal chamber housing 21 is not connected to injector chamber housing 11.

Figure 5B:
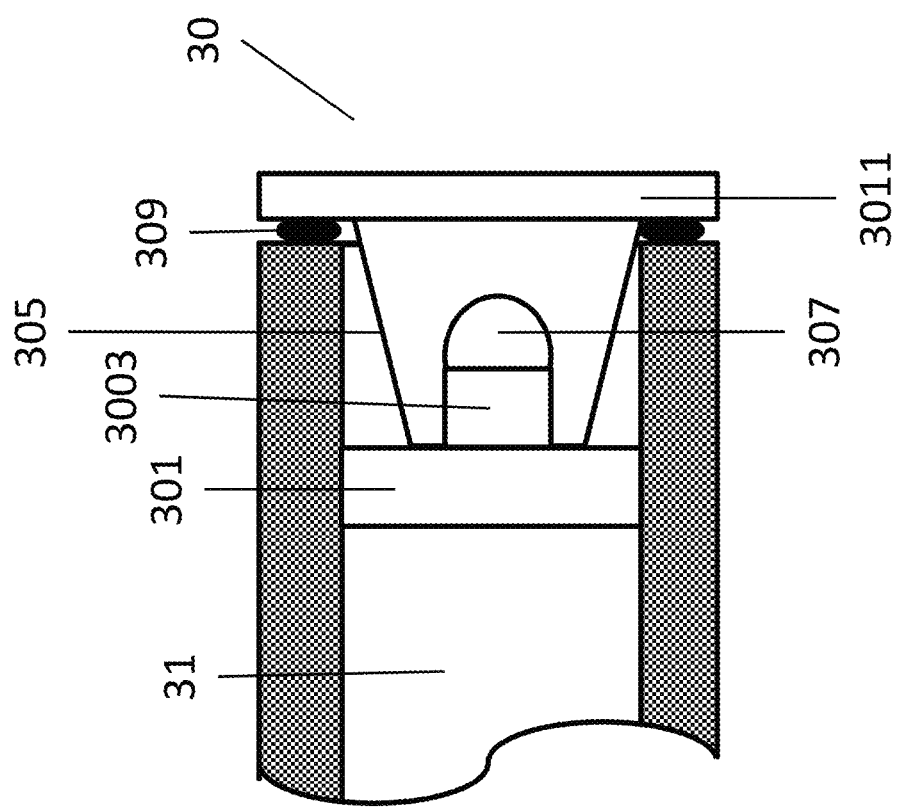
FIG. 5B shows a detailed illustrative cross-sectional view of the UVC LED module 30 placed within passway 31 in FIG. 5A.
Figure 9:
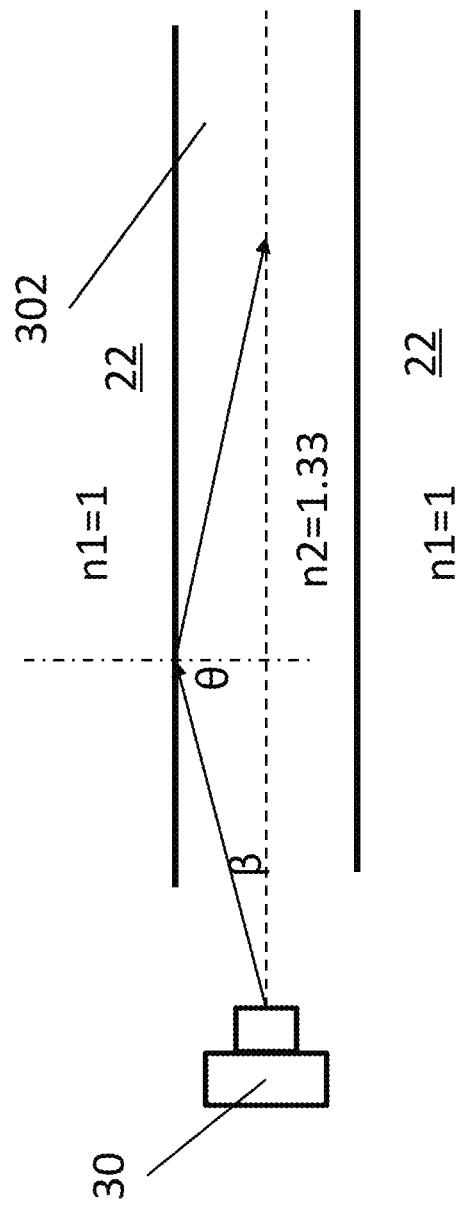
FIG. 9 illustrates the UVC light incident angle requirement for the UVC light to be totally confined within the flowing fluid (water) pillar.

UVC LED module 30 is placed within UVC LED module passway 31, which is surrounded by injector chamber housing 11. The emitting surface of UVC LED module 30 is immersed in the fluid within outlet chamber 15 facing nozzle 16, coupling the UVC light emissions into laminar flow pillar 302. UVC LED module passway 31 houses UVC LED module 30 and ensures coupling of the UVC emissions into laminar flowing fluid pillar 302 while makes electrically insulation from the fluid within injector chamber housing 11. In general, a fluid such water tight or air tight UVC transparent window, such as a quartz window, can ensure the optical coupling and electrically insulation discussed here. FIG. 5B shows a detailed illustrative cross-sectional view of UVC LED module 30 placed within passway 31 in FIG. 5A. As shown, UVC LED module 30 contains an electrical circuit board and/or heat sink 301, a UV LED light source 3003 containing one or an array of UV LEDs emitting UVB or UVC light, a UV lens 307 for enhancing UV light extraction and improving light directionality, a UV reflective bowl 305 for further enhancing UV light extraction and improving light directionality, and a UV transparent window 3011. UVC LED module 30 can be fixed onto the wall of UVC LED module passway 31, and UV LED light source 3003 is bonded onto electrical circuit board/heat sink 301 for electrical functionalities and heat removal. If using a hemisphere lens for UV lens 307, UV light emission angle can be within 70°. Referring to FIG. 9 this means the angle β there can be less than 35°, good for total internal reflection in the case where laminar flowing pillar 302 is water pillar and air spacer 22 is air. Lens 307 and window 3011 can be made of UV transparent materials such as quartz, sapphire, or AlN, et al. The UV reflective bowl 305 can be a parabolic bowl or the like with the inner surface coated by UV reflective material such as metal aluminum with $SiO_2$ coating protection. Window 3011 is in contact with fluid in outlet chamber 15, and transmits UV light into the fluid in outlet chamber 15 and laminar flowing fluid pillar 302. Further, window 3011 is in fluid-tight such as water-tight connection to UVC LED module passway 31, through a rubber O-ring 309, tightly pressed by window 3011 onto the wall of UVC LED module passway 31, as shown in FIG. 5B. Window 3011 and UVC LED module passway 31 thus allow for optical coupling and electrical insulation between UVC LED module and the fluid within injector chamber housing 11.

If the emission from UVC LED module 30 is relatively directional, the difference of refractive indices of laminar flowing fluid pillar 302 and air spacer 22 will confine UVC emissions within laminar flowing fluid pillar 302. This innovative design maximizes UVC light path length and minimizes UVC light loss. The principle of the light confinement within laminar flowing fluid pillar 302 is explained in FIG. 9. As shown, taking water as an exemplar fluid, the laminar flowing fluid pillar 302 will have water's refractive index ($n_2$=1.33), and the surrounding air spacer 22 has a refractive index equal to 1 ($n_1$=1). So, if the light incident angle θ to the water/air interface is larger than a critical incident angle $θ_c$, where $θ_c$=arcsine($n_1/n_2$)=48.75°, the light ray will be subjected to total internal reflection, resulting in a total confinement of the light ray within laminar flowing fluid pillar 302. To satisfy incident angle $θ>θ_c$=48.75°, the light emitting angle β shown in FIG. 9 has to satisfy $β<β_c$=90-arcsine($m/n_2$)=41.25°, where $β_c$ is defined as the critical light emitting angle. This is normally easy to achieve via suitable package technologies to the UVC LED module 30, such as adding a hemisphere lens to the UVC LEDs used for the UVC LED module 30.

Further, UVC LED module 30 may also include a flow sensor, to turn on the UVC LEDs 3003 in module 30 when sensing a fluid flow. For example, a flow sensor may be placed within outlet chamber 15, with its electrical connections fluid-tight such as water-tight wired to electrical circuit board/heat sink 301 to signal UVC LED module 30 on/off. It may also include a UV detector, to detect UVC radiance so as to feedback to ensure desired UVC light intensity. For example, a UV detector may be placed within outlet chamber 15, with its electrical connections fluid-tight such as water-tight wired to electrical circuit board/heat sink 301 to signal UVC LED module 30 to adjust its output power.

Now let us discuss a few scenarios for different light emitting angle β. Referring to FIG. 5 and FIG. 9, if the light emitting angle β equals to zero, the light will obviously be fully confined within laminar flowing fluid pillar 302, and the light path length will be the same as the length of laminar flow pillar 302. If $0<\beta<\beta_c$, the UVC light will still be fully trapped within laminar flow pillar 302, however the light ray will be bouncing between upper and lower fluid/air interfaces by total internal reflection, gaining an enlarged light path length by a factor of $$\frac{1}{\cos\beta}$$

compared with a straight-line light path length L as calculated in eq #2. Taking water pillar as an example, and suppose the light emitting angle β=40°, this will lead the light path length to be 1.3 times of the straight line light path length L as calculated in eq #2. According to the teachings given in FIG. 4, this enlarged light path length will deliver more UVC dosage to the fluid and result in better germicidal effect. When β=0, for a preset UV dosage experienced by the flowing fluid pillar 302, J, the length of the flowing fluid pillar 302 theoretically should be equal to the light path length L as calculated in eq #2. If the length of the flowing fluid pillar is less than the light path length L as calculated in eq #2, the UV dosage will be less than the preset UV dosage. If the length of the flowing fluid pillar is larger than the light path length L as calculated in eq #2, the UV dosage will be more than the preset UV dosage. In this case, the length of the flowing fluid pillar can be designed to be equal to or larger than the light path length L as calculated in eq #2 so as to achieve a desired UV dosage. When $0<\beta<\beta_c$, for a preset UV dosage experienced by the flowing fluid pillar 302, J, the light path length becomes $$\left(\frac{1}{\cos\beta}\right)L,$$

the length of the flowing fluid pillar 302 can be less than L while still achieving the preset UV dosage due to the enhanced delivery of UV dosage by the enlarged light path length. For $\beta>\beta_c$, the UVC light will no longer be fully trapped within laminar flowing fluid pillar 302, it will exit the fluid/air interface and enter into air spacer 22. In this case, if the inner surface of germicidal chamber housing 21 is coated with UVC mirror or reflector (this mirror is not shown in FIG. 5), the ray will be bouncing between the upper and lower inner surfaces of germicidal housing 21. This scenario still has the potential to enlarge the light path length by a factor of $$\frac{1}{\cos\beta} \text{ (if } \beta = 60°,$$

the light path length within laminar flowing fluid pillar 302 would be doubled; if β=80°, it would be 5.76 times!), however, since practically any UVC mirror could only reflect 90%-95% of the incident light, a lot of UVC light power would be waisted, as makes this scenario not the mostly preferred in the present invention (For example, for a UVC mirror of 90% reflectivity, bouncing 20 times would waste ~88% of the original incident UVC light power.).

Shown in FIG. 5, germicidal chamber housing 21 can be transparent such as made of glass or transparent plastics or has a transparent window, so that laminar flowing fluid pillar 302 coupled with UVC light can be viewed by operator. Also, as discussed above, the designed light path length L calculated via eq #2 can be equal to or larger than the length of laminar flowing fluid pillar 302. The inlet flow rate and the minimum aperture cross-sectional area of nozzle 16 (which determines the cross-section of laminar flowing fluid pillar 302) can be used to tune the length of laminar flowing fluid pillar 302. For example, if inlet flow rate is 1 gallon/min, and the diameter of laminar flowing fluid pillar 302 is 0.5 inch, then the flow velocity of fluid in laminar flowing fluid pillar 302 will be 49.8 cm/s; if the inlet flow rate is 10 gallon/min, then the fluid velocity in laminar flowing fluid pillar 302 will be 498 cm/s. Disinfector M1 shown in FIG. 5A can be preferably mounted vertically, so that laminar flowing fluid pillar 302 is straight and the disinfected fluid flows out fluid outlet 2 to service various purposes.

To summarize, fluid laminar flow injector 10 is used to create laminar flowing fluid pillar 302, and UVC light from UVC LED module 30 is coupled and preferably totally confined into laminar flowing fluid pillar 302 for maximum usage of UVC light for germicidal effect. The length of germicidal chamber 20 is longer enough to house a designed light path length of laminar flowing fluid pillar 302, whose length is determined by the flow rate and design of fluid laminar flow injector 10. Depending on the required disinfection flow rate, the designed length of laminar flowing fluid pillar 302 can be within 10 to a few hundred of centimeters, for example, from 10-500 cm, or from 20-400 cm, or from 50-300 cm. Also, depending on the required disinfection flow rate, other dimensions of disinfector module M1 can be engineered and fine-tuned. The cores to the present invention are: 1) to calculated the desired light path length for given disinfection flow rate, UVC disinfection power, UVC absorption coefficient, and target UVC dosage (using eq #2); 2) to design the disinfector module to form desired length laminar flowing pillar 302, and 3) to couple and confine the UVC emissions into laminar flowing pillar 302.

Figure 6:
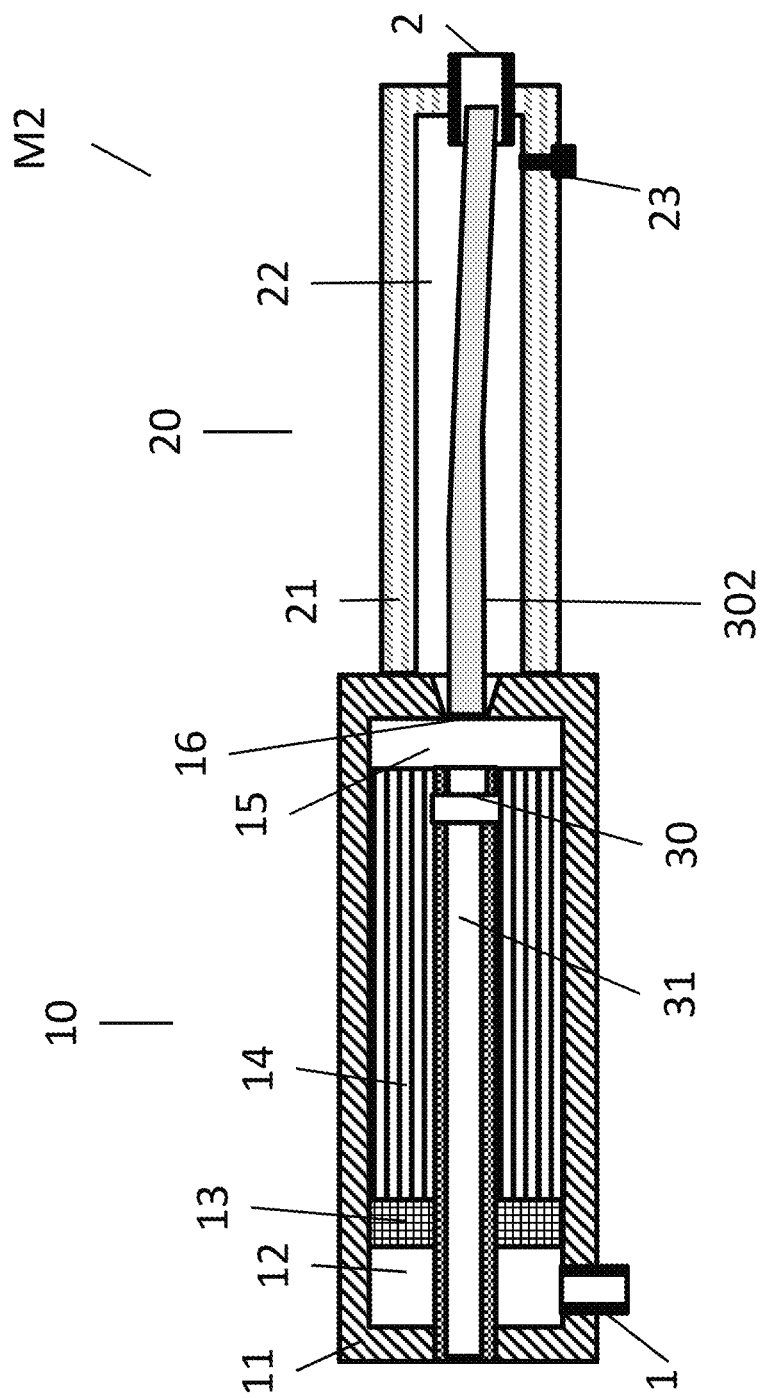
FIG. 6 shows an illustrative cross-sectional view of a flowing fluid UV disinfector module according to an embodiment of the present invention.

When mounted horizontally, laminar flowing fluid pillar 302 may be bended by gravity. In this scenario, a disinfector module M2 is illustrated in FIG. 6, wherein fluid outlet 2 is displaced to accommodate the gravity bending displacement of laminar flowing fluid pillar 302. Further, a drainage 23 may be added to germicidal chamber 20. For example, if inlet flow rate is 1 gallon/min, and the diameter of laminar flowing fluid pillar 302 is 0.5 inch, then the (horizontal) flow velocity of fluid in laminar flowing fluid pillar 302 will be 49.8 cm/s, which means that if the horizontal length of laminar flowing fluid pillar 302 is 49.8 cm, it will be vertically bended by gravity to a distance of 4.9 m ($\frac{1}{2}gt^2$). In this small flow case, the disinfector module is preferred to be mounted vertically instead of horizontally. For large flow rates, for example, if the inlet flow rate is 10 gallon/min, still with a 0.5-inch diameter of laminar flowing fluid pillar 302 then the (horizontal) fluid velocity in laminar flowing fluid pillar 302 will be 498 cm/s, which means that if the horizontal length of laminar flowing fluid pillar 302 is 49.8 cm, it will be vertically bended by gravity only to a distance of 4.9 cm. So, basically, for large flow rates disinfector modules can be mounted horizontally.

Figure 7:
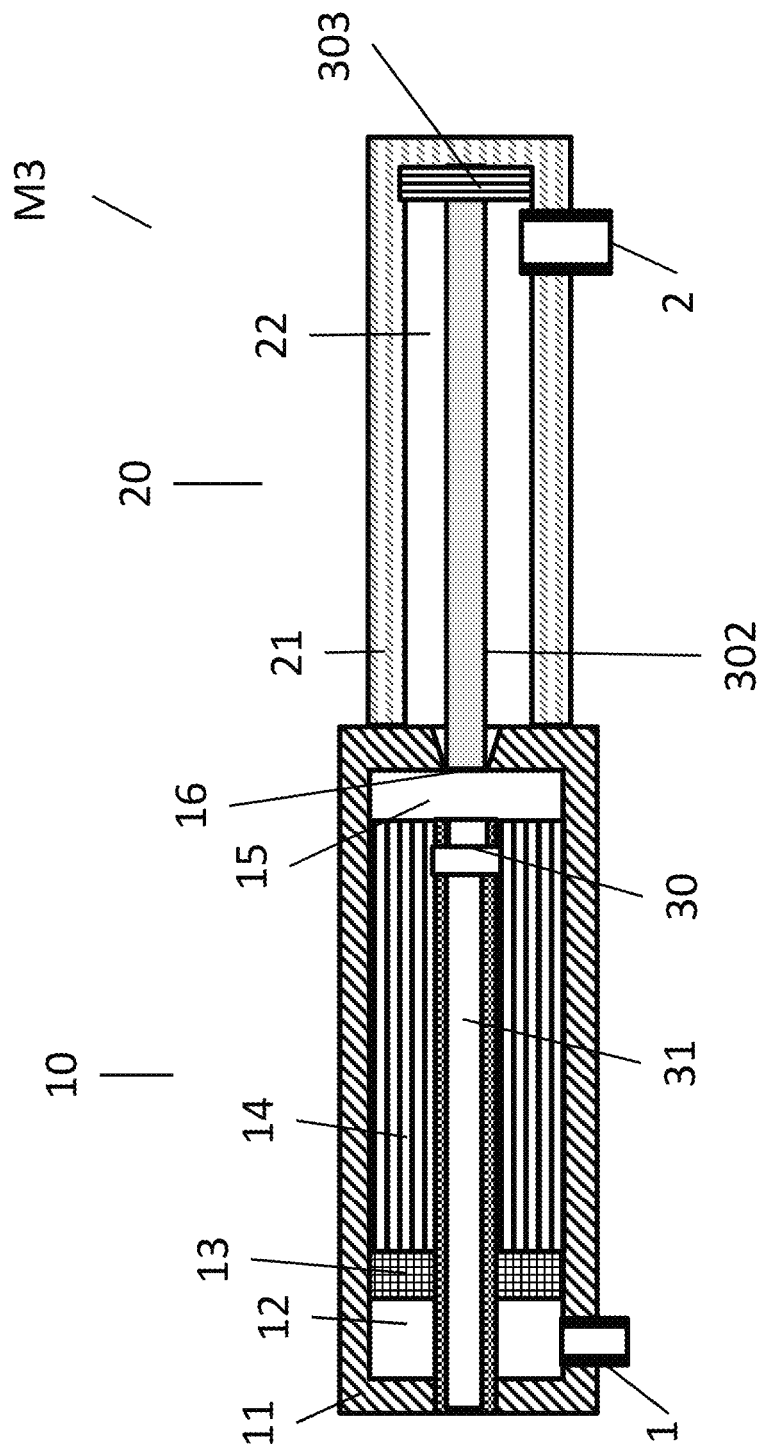
FIG. 7 shows an illustrative cross-sectional view of a flowing fluid UV disinfector module according to an embodiment of the present invention.

In another embodiment, the light path length L may be significantly larger than the length of laminar flowing fluid pillar 302. This is illustrated in disinfector module M3 shown in FIG. 7. A UVC mirror 303 is placed at the bottom of germicidal chamber 20, perpendicularly facing up to the UVC light coupled laminar flowing fluid pillar 302. Fluid will flow out through fluid outlet 2, and a large amount of UVC light will be reflected back to laminar flowing fluid pillar 302. This embodiment will further enhance the germicidal effect. UVC mirror 303 can also be replaced by a UVC reflective film.

Figure 8:
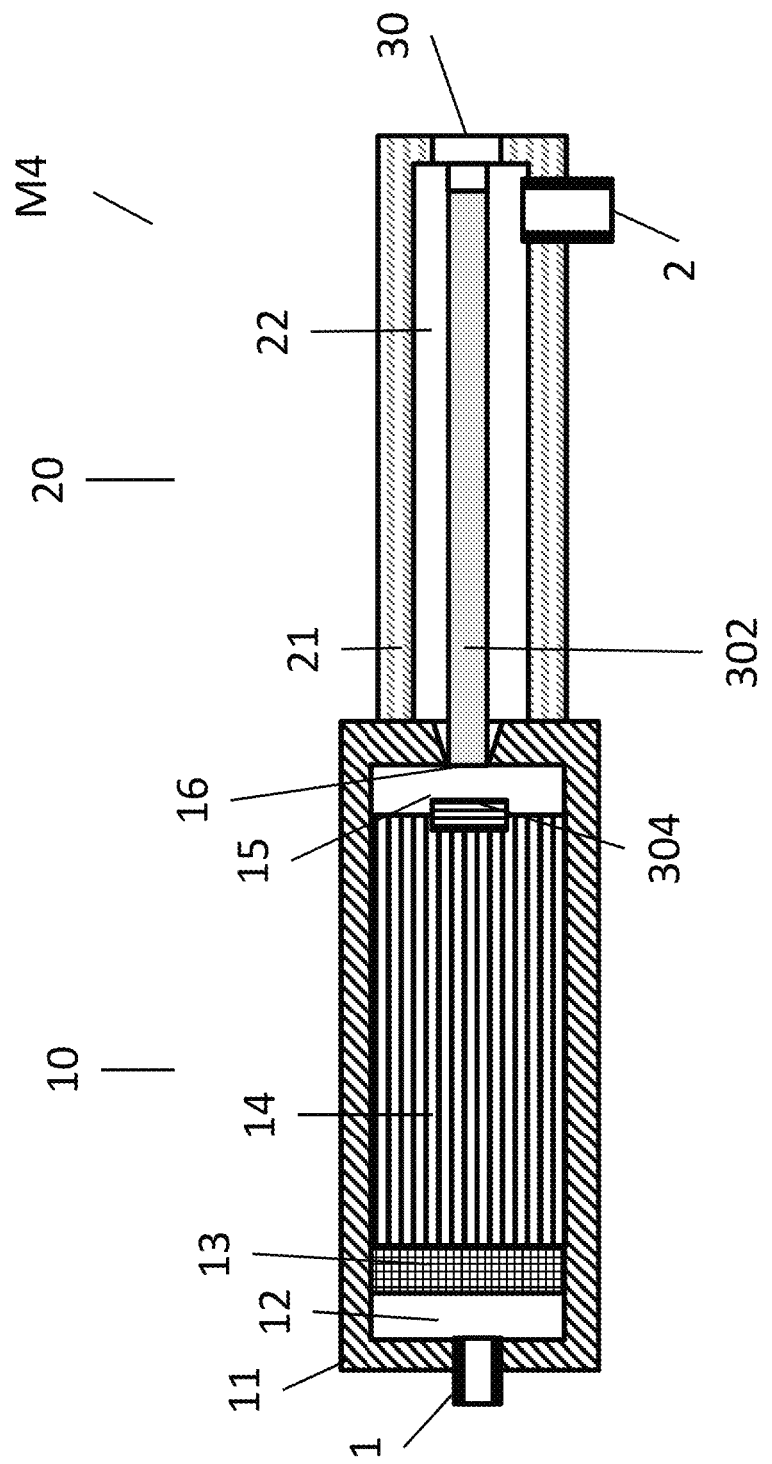
FIG. 8 shows an illustrative cross-sectional view of a flowing fluid UV disinfector module according to an embodiment of the present invention.

UVC LED module 30 can also be placed at the bottom of germicidal chamber 20, facing against laminar flowing fluid pillar 302, as shown in the embodiment illustrated in FIG. 8. In the embodiment shown in FIG. 8, the electrical insulation is achieved without a UVC LED module passway 31, since UVC LED module 30 can be water/air tight mounted into germicidal chamber housing 21. Optionally, a UVC mirror or UVC reflective film 304 can be placed within outlet chamber 15, facing against UVC LED module 30 to bounce back UVC light for enhanced light path length.

In embodiments according to the present invention, the light emitting surface of UVC LED module 30 (3011) and UVC mirror or UVC reflection film 303, 304 need to be cleaned if fluid sediments formed on these two surfaces. Other surfaces do not contact with UVC light so basically are maintenance free.

The present invention has been described using exemplary embodiments. However, it is to be understood that the scope of the present invention is not limited to the disclosed embodiments. On the contrary, it is intended to cover various modifications and similar arrangement or equivalents which can be obtained by a person skilled in the art without creative work or undue experimentation. The scope of the claims, therefore, should be accorded the broadest interpretation so as to encompass all such modifications and similar arrangements and equivalents.

What is claimed is:

1. A method for disinfecting a fluid, comprising:
   providing a fluid to be disinfected;
   generating a flowing fluid pillar of the fluid to be disinfected, wherein the flowing fluid pillar is completely surrounded, along an axial direction, by and in direct contact with a fluid medium having a refractive index lower than that of the fluid to be disinfected;
   emitting UV light into the flowing fluid pillar along the axial direction of the flowing fluid pillar;
   determining a light path length of the UV light, L, according to the following equation:

$$L = -\frac{1}{\alpha} \ln\left(1 - \frac{J\alpha G}{P}\right)$$

where $\alpha$ is UV light absorption coefficient of the fluid to be disinfected, G is flow rate of the flowing fluid pillar, P is input UV light power of the UV light impinging substantially vertically to a cross-section of the flowing fluid pillar, J is UV dosage experienced by the fluid in the flowing fluid pillar; and
   determining a length of the flowing fluid pillar according to the light path length of the UV light.

2. The method for disinfecting a fluid according to claim 1, wherein the fluid medium is air or vacuum.

3. The method for disinfecting a fluid according to claim 1, wherein the flowing fluid pillar is a laminar flow pillar.

4. The method for disinfecting a fluid according to claim 1, wherein the flowing fluid pillar is generated flowing downward.

5. The method for disinfecting a fluid according to claim 1, wherein, when $\beta=0$, where $\beta$ is the emitting angle of the UV light, the length of the flowing fluid pillar is selected to be equal to or larger than the light path length of the UV light.

6. The method for disinfecting a fluid according to claim 1, wherein, when $0<\beta<\beta_c$, where $\beta$ is the emitting angle of the UV light and $\beta_c$ is the critical light emitting angle, the path length of the UV light becomes $$\left(\frac{1}{\cos\beta}\right)L,$$

the length of the flowing fluid pillar is selected to be equal to or larger than L.

7. The method for disinfecting a fluid according to claim 1, wherein the fluid is water.

8. The method for disinfecting a fluid according to claim 1, wherein the UV light source is an AlGaN based UVB or UVC LED light source.

9. The method for disinfecting a fluid according to claim 1, wherein a length of the flowing fluid pillar is in the range of 10 to 500 cm.

10. The method for disinfecting a fluid according to claim 1, wherein a power of the emitted UV light is in the range of 30-70 mW and a flow rate of the flowing fluid pillar is in the range of 0.5-1.5 gallon/min; a power of the emitted UV light is in the range of 300-700 mW and a flow rate of the flowing fluid pillar is in the range of 5-15 gallon/min; or a power of the emitted UV light is in the range of 3-7 watts and a flow rate of the flowing fluid pillar is in the range of 50-150 gallon/min; or a power of the emitted UV light is in the range of 30-70 watts and a flow rate of the flowing fluid pillar is in the range of 500-1500 gallon/min.

* * * * *